United States Patent
Choudhary et al.

(10) Patent No.: US 6,828,463 B2
(45) Date of Patent: Dec. 7, 2004

(54) PROCESS FOR THE PREPARATION OF CARBONYL COMPOUNDS WITH A CARBONYL GROUP ATTACHED TO THE AROMATIC RING

(75) Inventors: Vasant R. Choudhary, Maharashtra (IN); Vijay S. Narkhede, Maharashtra (IN); Jayant R. Indurkar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,358

(22) Filed: Mar. 26, 2003

(65) Prior Publication Data

US 2004/0192972 A1 Sep. 30, 2004

(51) Int. Cl.$^7$ .............................................. C07C 45/27
(52) U.S. Cl. ...................... 568/320; 568/321; 568/332; 568/335
(58) Field of Search ................................ 568/320, 321, 568/332, 335

(56) References Cited

U.S. PATENT DOCUMENTS

| | | | |
|---|---|---|---|
| 4,275,241 A | 6/1981 | Bohm et al. ................ | 568/426 |
| 4,366,325 A | 12/1982 | Wedemeyer et al. ........ | 568/432 |
| 4,839,323 A | 6/1989 | Goe et al. .................... | 502/159 |
| 4,950,794 A | 8/1990 | Candela et al. ............ | 568/320 |
| 5,298,664 A | 3/1994 | Rains et al. ................ | 568/323 |
| 5,476,970 A | 12/1995 | Rains et al. ................ | 568/323 |
| 5,723,676 A | 3/1998 | DeWitt et al. .............. | 568/323 |
| 6,437,191 B1 | 8/2002 | Choudhary et al. ......... | 568/319 |
| 6,506,932 B2 * | 1/2003 | Sumida et al. .............. | 562/412 |

FOREIGN PATENT DOCUMENTS

| | | |
|---|---|---|
| FR | 2 745 287 | 8/1997 |
| FR | 2 768 728 | 3/1999 |
| FR | 2 768 729 | 3/1999 |
| JP | A 64-89894 | 4/1989 |
| JP | A 2-59205 | 2/1990 |
| JP | A 8-277241 | 10/1996 |
| JP | A 2000-86570 | 3/2000 |

OTHER PUBLICATIONS

Khenkin et al. Oxygen Transfer from Sulfoxides: Oxidation of Alkylarenes Catalyzed by a Polyoxomolybdate, [PMo12O40]3–. Journal of the American Chemical Society, 2002, vol. 124 p 4198–4199.*

I.W.C.E. Arends et al.; "Activities and Stabilities of Heterogeneous Catalysts in Selective Liquid Phase Oxidations: Recent Developments"; Applied Catalysis A: General 212; 2001; pp 175–187.

Grorge A. Olah; "Friedel–Crafts and Related Reactions"; Interscience Publishers; 1964; pp 1003–1032.

* cited by examiner

Primary Examiner—Samuel Barts
Assistant Examiner—Sikarl A. Witherspoon
(74) Attorney, Agent, or Firm—Oliff & Berridge, PLC

(57) ABSTRACT

The present invention relates to a process for the preparation of aromatic carbonyl compound with carbonyl group attached to its aromatic ring, particularly relates to a process for the preparation of aromatic carbonyl compound with carbonyl group attached to its aromatic ring, by oxidizing with molecular oxygen the methylene or alcoholic group attached to aromatic ring of an aromatic compound, using a polyoxotnetallate(s) anion exchanged hydrotalcite catalyst.

22 Claims, No Drawings

PROCESS FOR THE PREPARATION OF CARBONYL COMPOUNDS WITH A CARBONYL GROUP ATTACHED TO THE AROMATIC RING

TECHNICAL FIELD

The present invention relates to a process for the preparation of aromatic carbonyl compound with carbonyl group attached to its aromatic ring. The present invention particularly relates to a process for the preparation of aromatic carbonyl compound with carbonyl group attached to its aromatic ring, by oxidizing with molecular oxygen the methylene or alcoholic group attached to aromatic ring of an aromatic compound, using a polyoxometallate(s) anion exchanged hydrotalcite catalyst.

Background Art

Aromatic carbonyl compounds, such as phenones and aromatic aldehydes are industrially important chemicals, used as organic intermediates for the production pharmaceuticals and perfumery chemicals.

A number of processes are known in the prior art for the preparation of aromatic carbonyl compounds.

Friedel-Crafts Acylation Processes

Both the homogeneous and heterogeneous liquid phase processes based on Friedel-Crafts type reactions for the preparation of aromatic carbonyl compounds, particularly aromatic ketones by acylation of aromatic compounds are known in the prior art.

Friedel-Crafts Acylation Reactions Catalyzed by Homogeneous Catalysts

The Friedel-Crafts type acylation of aromatic compounds by various acylating agents, using homogeneous Lewis acid catalysts, such as $AlCl_3$, $BF_3$, $ZnCl_2$ and other metal chlorides and protonic acid catalysts, such as $H_2SO_4$, $H_3PO_4$, HF, etc., are well known in the prior art [ref. G. A. Olah, in Friedel-Crafts and related reactions: vol. III, Acylation and related reactions, Wiley-Interscience Publ., New York, 1964].

In a US patent [U.S. Pat. No. 5,476,970 (1995)], Rains et al. disclosed a homogeneous liquid phase process for the acylation of $R_1R_2C_6H_4$ by $R_3R_4C_6H_3COCl$, wherein $R_1$, $R_2$, $R_3$ and $R_4$ are chemical groups, using $FeCl_3$ catalyst at high pressures.

A US patent [U.S. Pat. No. 5,298,664 (1994)] discloses the production of aryl ketones by reaction of aromatic hydrocarbon compounds and aromatic or aliphatic alkyl halides in the presence of anhydride iron (III) chloride.

In French patents [FR 2,768,728 (1999) and FR 2,768,729 (1999)], Baudry et al. disclosed liquid phase homogeneous process for the benzoylation of anisole by benzoyl chloride using rare earth halides or uranyl halide.

In a Japanese patent [JP 08,277,241, A2 (1996)] Kunikata disclosed a liquid phase process for the acylation of phenol by phenyl acetyl chloride using a homogeneous $AlCl_3$ catalyst. A use of $AlCl_3$ as a homogeneous catalyst is also disclosed by Ono for the acylation of toluene with acetyl chloride at high pressure in a Japanese patent [JP 09,059, 205, A2 (1997)].

In a very recent Japanese patent [JP 2,000,086,570, A2 (2000)] Shoji et al. have disclosed a homogeneous liquid phase process for the acylation of toluene by acetyl fluoride using $HF$-$BF_3$ as a catalyst.

The main disadvantages of the Friedel-Crafts acylation processes based on the use of above mentioned homogeneous acid catalysts for the preparation of aromatic ketones are as follows:

1) The separation and recovery of the dissolved acid catalysts from the liquid reaction mixture is difficult.
2) The disposal of the used acid catalysts creates environmental pollution.
3) The homogeneous acid catalysts also pose several other problems such as high toxicity, corrosion, spent acid disposal and use of more than the stoichiometric amount.

Friedel-Crafts Type Acylation Catalyzed by Heterogeneous Solid Catalysts

A few liquid phase processes for the acylation of aromatic compounds by acyl halides using solid catalysts are known in the prior art.

In a Japanese patent [JP 01,089,894, A2 (1995)], Miyata e al. disclosed a liquid phase process for the acylation of toluene with benzoyl chloride using ammionium chloride treated H-beta zeolite catalyst under reflux for 3 h to get para-acylated toluene with 28% yield.

In a recent French patent [FR 2,745,287, A1 (1997)], Barbier et al. disclosed liquid phase acylation of anisole by benzoyl chloride under reflux using neodymium chloride deposited on montmorillonite K-10 clay.

Very recently, in a US patent [U.S. Pat. No. 6,437,191 (2002)], Choudhary et al. disclosed a process for the acylation aromatic compounds by acyl halides to corresponding aryl ketones, using a reusable solid catalyst comprising indium halide.

In the above processes, involving use of solid catalysts, most of the limitations of the homogenous catalyzed Friedel-Crafts acylation processes are eliminated. However these processes also suffer because of the formation of hydrogen halide, which highly corrosive and toxic in nature. Because of the formation of hydrogen halide, these processes are also not environmentally benign. Other limitation of the Friedel-Crafts acylation processes is that the acylating agents used for the acylation of aromatic compounds are quite costly. Hence there is need to develop a better process for the preparation of aromatic carbonyl compounds, which is environmentally more benign and requires low cost feeds, such as that based on the oxidation of aromatic hydrocarbons and alcohols.

Processes for the Preparation of Aromatic Carbonyl Compounds by Oxidation of Aromatic Compounds A few processes based on the oxidation of aromatic compounds for the preparation of the aromatic carbonyl compounds are also known in the prior art.

In a US patent [U.S. Pat. No. 5,723,676 (1998)] DeWitt, et al have disclosed a process for producing benzophenone by reacting diphenyl methane with manganese dioxide in the presence of a strong acid. This process involves a stoichiometric reaction between diphenyl methane, manganese dioxide and a strong acid, which is highly corrosive, and hence produces a large volume of toxic and corrosive waste.

A US patent [U.S. Pat. No. 4,275,241 (1981)] discloses a process for the preparation of a 3-phenoxy benzaldehyde by contacting 3-phenoxy benzyl alcohol with an aqueous solution of a dichromate and sulphuric acid. This process also involves a stoichiometric reaction between the aromatic alcohol and the dichromate in the presence of sulphuric acid and thereby producing a large volume of toxic and corrosive waste.

A use of molecular oxygen as an oxidizing agent for the oxidation of aromatic compounds in the preparation of aromatic carbonyl compounds is also disclosed in the prior art, as follows.

In a US patent [U.S. Pat. No. 4,366,325 (1982)] Wedemeyer, et al have disclosed a process for the oxidation of 3-phenoxy-benzyl alcohol by oxygen to 3-phenoxybenzaldehyde using a platinum metal catalyst in aqueous alkali in the presence of lead and/or tellurium and/or bismuth. Because of the aqueous alkali solution, the reaction mixture is corrosive and a corrosive waste is produced in the process.

A US patent [U.S. Pat. No. 4,950,794(1990)] discloses a liquid phase process for the oxidation of ethyl benzene by molecular oxygen to acetophenone and ethyl benzene hydro peroxide in the presence of alkali metal at the elevated temperature. In this process also, alkali metal containing wastewater is produced and also the selectivity for acetophenone is low.

In a US patent [U.S. Pat. No. 4,839,323 (1989)] Goe, et al have disclosed chromium salt bound on an insoluble polymer support as a catalyst for the oxidation with molecular oxygen of ethyl benzene to acetophenone, tetralin to α-tetralone, and 2-methyl-5-ethyl pyridine to 2-methyl-5-acetyl pyridine. However, the leaching of the chromium salt from the polymer is a serious problem (ref. Arends and Sheldon, Applied Catalysis, A: General Vol. 212, Page 175–187, and year 2001). Moreover, in this process, the catalyst shows good activity only at high pressures and temperatures. At the higher temperature and pressure, the oxidation process becomes more hazardous.

Because of limitations of the prior art processes there is great practical need for developing a better process for the preparation of aromatic carbonyl compounds, particularly involving the oxidation of aromatic compounds with molecular oxygen and using reusable solid catalyst having, high stability against leaching, high activity and high selectivity in the oxidation process, and also without using any solvent in the reaction so that the process is environmentally much more benign. This invention was, therefore, made to overcome the drawbacks or limitations of the prior art processes for the preparation of aromatic carbonyl compounds.

OBJECTS OF THE INVENTION

The main object of the invention is to provide a liquid phase catalytic process for the preparation of aromatic carbonyl compounds by oxidizing with molecular oxygen the methylene (—$CH_2$) or alcoholic (—CHOH—) group attached to aromatic ring of aromatic compounds to a carbonyl group (—CO—), using a solid catalyst.

An object of the invention is to provide a liquid phase oxidation process for the preparation of aromatic carbonyl compounds, which can be operated without any solvent and does not produced any corrosive and/or toxic by-product(s) and, hence, is environmentally benign.

Yet another object of this invention is to provide a catalytic oxidation process for the preparation of aromatic carbonyl compounds, which can be operated even at or close atmospheric pressure and, hence, is less hazardous.

SUMMARY OF THE INVENTION

The present invention relates to a process for the preparation of aromatic carbonyl compound with carbonyl group attached to its aromatic ring. The present invention particularly relates to a process for the preparation of aromatic carbonyl compound with carbonyl group attached to its aromatic ring, by oxidizing with molecular oxygen the methylene or alcoholic group attached to aromatic ring of an aromatic compound, using a polyoxometallate(s) anion exchanged hydrotalcite catalyst.

DETAILED DESCRIPTION OF THE INVENTION

Accordingly the present invention provides a process for the preparation of aromatic carbonyl compounds of general formula (I)

Ar—CO—R            Formula (I)

Ar represents an aromatic nucleus with one or more aromatic rings

R is defined as hydrogen group (—H), paraffine group (—$C_nH_{2n+1}$) wherein, n is an integer more than or equal to 1), substituted paraffine groups, cycloparaffine group (—$C_mH_{2m-1}$) wherein, m is an integer greater than 2), substituted cycloparaffine group, substituted or unsubstituted aromatic nucleus containing one or more aromatic rings.

by liquid phase catalytic oxidation, said process comprising the steps of:

(a) pretreating catalyst (III) (the polyoxometallate anion exchanged hydrotalcite catalyst) under vacuum or gas atmosphere free from traces of moisture and carbon-dioxide at a temperature in the range 50–200° C., for a period sufficient to remove adsorbed moisture from the catalyst;

(b) oxidizing aromatic compound of general formula (II) with the pretreated hydrotalcite catalyst of step (a)

Ar—CHX—R            Formula (II)

wherein,

Ar and R are as defined above

X is hydrogen group (—H) or hydroxyl (—OH) group, (c) separating the products (I) from the reaction mixture;

(d) washing the used catalyst by aromatic compound (II) or optionally washing the catalyst by non aqueous solvent and drying the washed catalyst; and (e) recycling the catalyst for subsequent reaction batch.

An embodiment of the present invention, wherein in step (b) the hydrotalcite catalyst anions are obtained from a hydrotalcite catalyst (IV) represented by a general formula:

$[(M^{2+})_{1-x}(M^{3+})_x(OH)_2]^{x+}(A^{n-})_{x/n} \cdot qH_2O$            Formula (IV)

wherein $M^{2+}$ is divalent metal cation, $M^{3+}$ is trivalent metal cation, x is mole fraction of $M^{3+}$ between $M^{2+}$ and $M^{3+}$ in the range of 0.06–0.4, $A^{n-}$ is anion selected from $CO_3^{2-}$, $OH^{1-}$, $Cl^{1-}$, $NO_3^{1-}$ or a mixture thereof, n is an integer showing number of negative charges on the anion ($A^{n-}$)

q is number of water molecules, by (a) replacing the $A^{n-}$ anions from said hydrotalcite material (IV) at least partly by polyoxometallate anions in a gaseous atmosphere of oxygen, at a temperature in the range of 50–300° C. and pressure of about 1.0 atmosphere, in the presence of a solvent for a period of 1–100 hours;

(b) stirring the reaction mixture in a reactor and cooling the reactor temperature to about 30° C.;

(c) depressurizing the reactor; and (d) removing the catalyst (III) from the reaction mixture by filtration.

Another embodiment of the present invention, wherein polyoxometallate anions are selected from $(MnO_4)^{1-}$, $(Cr_2O_7)^{2-}$, $(CrO_4)^{2-}$, $(WO_4)^{2-}$, $(MoO^4)^{2-}$, $(SeO_4)^{2-}$, $(VO_3)^{1-}$, $(VO4)^{3-}$ or a mixture thereof.

Yet another embodiment of the present invention, wherein the concentration of the polyoxometallate anions in the catalyst is in the range from 0.05–5.0 mmol.g$^{-1}$.

Further embodiment of the present invention, wherein the usage of solvent is optional.

Still another embodiment of the present invention, wherein in step (b) the solvent and aromatic compound (II) weight ratio is in the range 0–50.

It is also an embodiment of the present invention, wherein in step (b) weight ratio of aromatic compound (II) with catalyst anions (III) is in the range 1:100.

Yet another embodiment of the present invention, wherein in step (b) continuous removal of water formed during oxidation of aromatic compound (II) is optional.

Further embodiment of the present invention, wherein in step (b) the stirring process in the reactor is done in batch mode or in semi-batch mode or in continuous mode.

It is also an embodiment of the present invention, wherein the reaction temperature in step (b) is in the range of 100–250° C.

Further embodiment of the present invention, wherein the reaction period in step (b) is in the range of 1–20 hours.

Yet another embodiment of the present invention, wherein the aromatic nucleus is selected from a group consisting of benzene, naphthalene, anthracene or phenanthrene.

Further embodiment of the present invention, wherein the aromatic nucleus may be substituted or unsubstituted.

Yet another embodiment of the present invention, wherein the substitution on the aromatic nucleus selected from the group consisting of paraffin ($C_nH_{2n+1}$) or substituted paraffin, cycloparaffin ($C_mH_{2m-1}$) or substituted cycloparaffin, phenyl ($C_6H_5$).

It is also an embodiment of the present invention, wherein substituted phenyl groups are selected from halo (F, Cl, Br or I), nitro ($NO_2$), hydroxyl (OH), ketonic (COR), sulfonic acid ($HSO_3$), alkoxy ($OC_nH_{2n+1}$), phenoxy ($OC6H_5$) or substituted phenoxy, ester ($COOC_nH_{2n+1}$), carboxylic acid (COOH), wherein n and m having values 1 or 2.

Still another embodiment of the present invention, wherein $M^{2+}$ in the hydrotalcite material (IV) is selected from $Mg^{2+}$, $Ni^{2+}$, $Co^{2+}$, $Cu^{2+}$, $Zn^{2+}$, $Mn^{2+}$, $Pd^{2+}$ or a mixture of thereof.

Further embodiment of the present invention, wherein $M^{2+}$ in the hydrotalcite material (IV) is $Mg^{2+}$, $Ni^{2+}$, $Co^{2+}$ or a mixture thereof.

It is also an embodiment of the present invention, wherein $M^{3+}$ in the hydrotalcite material (IV) is selected from $Al^{3+}$, $Fe^{3+}$, $Ga^{3+}$, $In^{3+}$, $Cr^{3+}$, $Ru^{3+}$ or a mixture thereof.

Further embodiment of the present invention, wherein $M^{3+}$ in the hydrotalcite-like material (IV) is $Al^{3+}$ or $Fe^{3+}$ or $Ga^{3+}$ or a mixture thereof.

It is also an embodiment of the present invention, wherein the mole fraction of $M^{3+}$ and x in the hydrotalcite material (IV) is in the range of 0.09 and 0.33.

Still another embodiment of the present invention, wherein the $A^{n-}$ anion in the hydrotalcite-like material (IV) is $CO_3^2$.

Yet another embodiment of the present invention, wherein the concentration of polyoxometallate anions in the hydrotalcite-like catalyst (III) is between 0.3 mmol.g$^{-1}$ and 4.0 mmol.g$^{-1}$.

The novel features of the present invention is further explained in the form of following preferred embodiments.

The catalyst (III) of the present invention shows high activity in the oxidation of aromatic compound (II) to corresponding aromatic carbonyl compound (I), even in the absence of any solvent, and hence the reaction temperature is low and/or the time required for obtaining the conversion of the aromatic compound (I) of practical interest, above about 20% is short.

Another embodiment of the present invention, wherein said solid catalyst can be separated easily, simply by filtration, and reused repeatedly in the process.

Still another embodiment of the present invention, wherein no toxic or corrosive by-product(s) is produced in the process and also the oxidation reaction in the process can be carried out even without using any solvent, and hence the process is environmentally benign.

Further embodiment of the present invention, wherein the oxidation reaction in the process can be carried out even at or close to atmospheric pressure and, hence, is less hazardous.

The process of this invention can be carried out in a stirred tank reactor, which is operated batch-wise with respect to the liquid reaction mixture consisting of said catalyst and said aromatic compound (II) to be oxidized with or without any non-aqueous solvent but operated batch-wise with decreasing pressure or semi-batch-wise with a constant or varying pressure or continuous manner at constant pressure with respect to the oxygen containing gas.

When X=H and R≠H

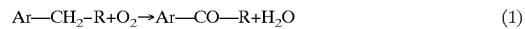

$$\text{Ar—CH}_2\text{-R} + O_2 \rightarrow \text{Ar—CO—R} + H_2O \qquad (1)$$

When X=OH and R=H

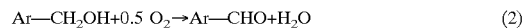

$$\text{Ar—CH}_2\text{OH} + 0.5\ O_2 \rightarrow \text{Ar—CHO} + H_2O \qquad (2)$$

When X=H and R≠H

$$\text{Ar—CHOH—R} + 0.5\ O_2 \rightarrow \text{Ar—CO—R} + H_2O \qquad (3)$$

The process of the invention may be carried out with or without using a non-aqueous solvent in step-ii of the process but the use of solvent is not preferred except when said aromatic compound (II) is normally solid. Examples of non-aqueous solvents, which may be used in the process of this invention, are liquid paraffinic hydrocarbons, benzene, toluene, xylenes, trimethyl benzenes, nitrobenzene, nitromethane, and the like. In the process of this invention, the role of the solvent is to dissolved solid reactant, said solid aromatic compound (II), or solid product and thereby to felicitated the reaction between the aromatic compound and oxygen over said catalyst (III). Normally, the solvent is not converted in the process of this invention.

The process of this invention may be carried out with or without continuous removal of the water formed in the oxidation reaction in step-ii of the process. The continuous removal of water during the reaction may be carried out, particularly when the normally liquid reactant, aromatic compound (II), or of the solvent, if used, in the process of this invention is water immiscible and has density lower than that of water and also has boiling point lower than that of the aromatic carbonyl compound. The removal of the reaction water is advantageous to increase the rate of the reaction. When the aromatic reactant, said the aromatic compound (II), is normally liquid and is water immiscible, the continuous removal of the reaction water can be effected by carrying out the oxidation under reflux and using a Dean-Stark trap between the reactor and the reflux condenser. When the aromatic reactant, said aromatic compound (II), is normally liquid having density very close to or higher than that of water or is normally solid, the continuous removal of the reaction water may be effected by using a non-aqueous water immiscible solvent having density lower than that of water and also having boiling point much lower than that of the aromatic reactant and reaction product and carrying out the oxidation under reflux using a Dean-Stark trap for the removal of the water from the refluxing water-solvent mixture. Use of Dean-stark trap or apparatus for removing water from refluxed water-water immiscible solvent mixture is well known in the prior art.

The role of the said catalyst (III) in the process of this invention is to catalyze the oxidation reaction between said aromatic compound and oxygen by activating both the reactants or at least one of the two reactants.

The pretreating of said catalyst (III) in step-i is essential to remove the traces of moisture present in the catalyst. Because of the presence of absorbed and/or adsorbed moisture the catalyst, shows lower activity in the process of this invention.

In the process of this invention, the catalytically active component(s) of said catalyst (III) is said polyoxometallate anions present at the anion exchange sites of said hydrotalcite-like catalyst (III); the polyoxometallate anions are immobilized by the attractive interaction of their negative charge with the positive charge present on double hydroxide layer of said hydrotalcite-like catalyst (III). Because of the strong attractive positive charge-negative charge interactions, the polyoxometallate anions are firmly held in said catalyst and there is no leaching of the polyoxometallate ions from said catalyst (III) during the oxidation reaction.

In the process of this invention, said catalyst (III) is heterogeneous with respect to the liquid reaction mixture and hence can be separated from reaction mixture by filtration and can also be reused repeatedly in the process without a much change in its activity for the oxidation.

In the process of this invention, the washing of used catalyst in step-iii is necessary to remove adsorbed and absorbed reaction species, reactants and products from the catalyst.

The present invention is described with respect to the following examples illustrating the process of this invention for the preparation of aromatic carbonyl compound by the oxidation of said aromatic compound (II) using said hydrotalcite-like catalyst (III). However, these examples are provided for illustrate purposes only and are not to be construed as limitations on scope of the process of this invention.

Definition of terms used in the examples

Conversion of reactant and selectivity of product in the process of this invention are defined as follows:

Conversion of reactant (%) mol % of the reactant converted in the process.

Selectivity of the product (%)=[(mol % of the reactant converted into the product)÷(mol % of the reactant converted into all the products)]×100.

Catalyst (III) is the polyoxometallate anions containing hydrotalcite catalyst of the process of this invention.

Aromatic compound (II) is said aromatic compound to be oxidized in the process of this invention.

II is aromatic compound (II).

III is catalyst (III).

I is said aromatic carbonyl compound (I) which is a main product of the process of this invention.

Example 1

This example illustrates the process of this invention for the oxidation of ethyl benzene to acetophenone using a hydrotalcite-like catalyst, containing 2.0 mmol $MnO_4^{1-}$ anions per gram of the catalyst, derived from a hydrotalcite-like material having a chemical formula:

$[(Mg^{2+})_{1-x}(Al^{3+})_x(OH)_2]^{x+}(CO_3^{2-})_{x/2} \cdot qH_2O$ wherein x=0.25.

The hydrotalcite-like material was prepared by adding simultaneously two aqueous solutions-solution-I containing 0.9 mol magnesium nitrate and 0.3 mol aluminum nitrate in 1000 ml deionized water and solution-II containing 3.05 mol potassium hydroxide and 0.23 mol potassium carbonate in 3000 ml deionized water, drop wise into a 10,000 ml flask containing 2000 ml deionized water under vigorous stirring at 40° C., while maintaining a constant pH of 11–12, which was monitored by means of a pH-meter. After the addition of both the solutions, the resulting precipitate was aged for 0.5 h and then filtered, thoroughly washed with deionized water and then dried at 80° C. under vacuum for 12 h and grinding the dried material to convert it into a fine powder.

The hydrotalcite-like catalyst was prepared from the hydrotalcite-like material by calcining 20 g of the hydrotalcite-like material at 600° C. for 4 h under static air and treating the calcined material with 500 ml aqueous solution containing 0.12 mol $KMnO_4$ under stirring at 80° C. for 1 h under nitrogen atmosphere and then filtering, washing with deionized water and drying the treated material under nitrogen atmosphere. The concentration of $MnO_4^{1-}$ anions in the dried catalyst was 2.0 $mmol.g^{-1}$.

Both the hydrotalcite-like material and the hydrotalcite-like catalyst have a structure similar to that of naturally occurring hydrotalcite-material (ref. Cavani, et al, Catalysis Today, Vol. 11, page 173–301, year 1991). The structure of both the solids was determined by X-ray diffraction using Cu-Kα radiation. The XRD data, 2θ value, and relative intensity of major XRD peaks of both the solids are as follows:

| For the hydrotalcite-like material | | | |
|---|---|---|---|
| 2θ (degree) | 11.0 | 22.2 | 34.0 |
| Relative intensity (%) | 100 | 54 | 30 |
| For the hydrotalcite-like catalyst | | | |
| 2θ (degree) | 11.0 | 22.2 | 34.0 |
| Relative intensity (%) | 100 | 54 | 30 |

The process for the oxidation of ethyl benzene (aromatic substrate) to acetophenone (aromatic carbonyl compound) using the hydrotalcite-like catalyst was carried out in the following steps.

STEP-I: The hydrotalcite-like catalyst was pretreated by heating it under vacuum at 150° C. for 2h.

STEP-II: Ethyl benzene and pure oxygen gas were contacted with the pretreated catalyst of mass 6 g in a magnetically stirred reactor of capacity 100 $cm^3$ provided with a reflux condenser, thermometer for measuring reaction temperature and an inlet for gaseous feed at the following reaction conditions:

| | |
|---|---|
| Aromatic substrate to catalyst weight ratio = | 10 |
| Solvent to aromatic substrate weight ratio = | Zero |
| Temperature = | 130° C. |
| Pressure = | 1.5 atm |
| Reaction period = | 10 h |

The oxidation reaction was carried out at constant pressure; the constant pressure was maintained by introducing oxygen in the reactor time-to-time from oxygen reservoir, using a fine needle value.

STEP-III: After the reaction, the reactor was cooled to room temperature and then it was depressurized. The reaction mixture was filtered to remove the solid catalyst. After removing the catalyst, the reaction mixture was analysed for the product(s) and unconverted aromatic substrate by gas chromatography, using thermal conductivity detector. The conversion and the product selectivity obtained were as follows.

Conversion of ethyl benzene : 65.3%
Selectivity for acetophenone : 98.0%

Examples 2–5

These examples further illustrate the repeated reuse of the catalyst of the process of this invention.

The catalyst prepared in Example-1, after its use in the oxidation reaction in Example-1, was washed with acetone and dried and then used in these examples repeatedly for the oxidation of ethyl benzene to acetophenone at the process conditions given in Table-I by the method similar to that described in Example-1. The results of the repeated use of the catalyst for the oxidation are given in Table-1.

TABLE 1

Results showing the repeated reuse of the catalyst in the oxidation of ethyl benzene in the process of this invention.

| Example No. | Example-2 | Example-3 | Example-4 | Example-5 |
|---|---|---|---|---|
| Catalyst (III) Used | Catalyst after use in Example-1 | Catalyst after use in Example-2 | Catalyst after use in Example-3 | Catalyst after use in Example-4 |
| Catalyst pre-treatment condition | Same as that in Example-1 | Same as that in Example-1 | Same as that in Example-1 | Same as that in Example-1 |
| Reactants | | | | |
| Aromatic compound (II) | Ethyl benzene | Ethyl benzene | Ethyl benzene | Ethyl benzene |
| Gas comprising oxygen | Pure oxygen | Pure oxygen | Pure oxygen | Pure oxygen |
| Reaction conditions | | | | |
| Solvent/II wt. ratio | 0.0 | 0.0 | 0.0 | 0.0 |
| II/III wt. Ratio | 11.1 | 12.1 | 12.5 | 12.9 |
| Temperature (° C.) | 130 | 130 | 130 | 130 |
| Pressure (atm) | 1.5 | 1.5 | 1.5 | 1.5 |
| Reaction period (h) | 10 | 10 | 10 | 10 |
| Main product i.e. Aromatic carbonyl compound (I) formed | Acetophenone | Acetophenone | Acetophenone | Acetophenone |
| Conversion of II (%) | 67.5 | 63.5 | 61.3 | 60.4 |
| Selectivity for I (%) | 97.9 | 98.1 | 98.3 | 98.5 |

Examples 6–9

These examples further illustrate the process of this invention for the oxidation of ethyl benzene to acetophenone at different reaction conditions, given in Table-2, using the catalyst prepared in Example-1 and by the method similar to that descried in Example-1, except that the reaction conditions are different. The results obtained are presented in Table 2.

TABLE 2

Results of the oxidation of ethyl benzene in the process of this invention.

| Example No. | Example-6 | Example-7 | Example-8 | Example-9 |
|---|---|---|---|---|
| Catalyst (III) Used | Catalyst prepared in Example-1 | Catalyst prepared in Example-1 | Catalyst prepared in Example-1 | Catalyst prepared in Example-1 |
| Catalyst pre-treatment condition | Same as that in Example-1 | Same as that in Example-1 | Same as that in Example-1 | Same as that in Example-1 |
| Reactants | | | | |
| Aromatic compound (II) | Ethyl benzene | Ethyl benzene | Ethyl benzene | Ethyl benzene |
| Gas comprising oxygen | Pure oxygen | Pure oxygen | Pure oxygen | Pure oxygen |
| Reaction conditions | | | | |
| Solvent/II wt. ratio | 0.0 | 0.0 | 0.0 | 0.0 |
| II/III wt. ratio | 10 | 10 | 10 | 10 |
| Temperature (° C.) | 130 | 130 | 105 | 120 |
| Pressure (atm) | 10 | 1.9 | 6.0 | 1.0 |
| Reaction period (h) | 20 | 5 | 1.5 | 20 |
| Main product i.e. Aromatic carbonyl compound (I) formed | Acetophenone | Acetophenone | Acetophenone | Acetophenone |
| Conversion of II (%) | 85.0 | 49.3 | 25.1 | 15.5 |
| Selectivity for I (%) | 97.5 | 99.1 | 99.8 | 99.5 |

Example 10

This example further illustrates the process of this invention for the oxidation of ethyl benzene to acetophenone using a hydrotalcite-like catalyst, containing $MnO_4^{1-}$ anions at concentration 0.4 mmol.g$^{-1}$, derived from a hydrotalcite-like material having chemical formula same as that in Example-1 except that x was 0.09 instead of 0.25.

The hydrotalcite-like material, with x=0.09, was prepared by the method similar to that described in Example-1 except that the amount of aluminum nitrate was 0.089 mol instead of 0.3 mol.

The hydrotalcite-like catalyst was prepared from the hydrotalcite-like material by the method similar to that described in Example-1 except that the amount of $KMnO_4$ was 0.01 mol instead of 0.12 mol. The concentration of $MnO_4^{1-}$ anions in the catalyst was 0.4 mmol.g$^{-1}$.

The XRD data of both the hydrotalcite-like material and the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-I. The conversion and product selectivity were as follows.

Conversion of ethyl benzene : 40.2%
Selectivity for acetophenone : 99.0%

Examples 11–18

These examples further illustrate the process of this invention for the oxidation of diphenyl methane to benzophenone, n-propyl benzene to propiophenone, n-butyl benzene to n-butyrophenone 4-ethyl toluene to 4-methyl acetophenone and benzhydrol to benzophenone at different reaction conditions.

The oxidation reactions were carried out using the catalyst prepared in Example-10 and by the method similar to that described in Example-1 except that the reaction conditions are different.

The results obtained at different reaction conditions are given in Tables 3 and 4.

TABLE 3

Results of the oxidation of said aromatic compound (II) in the process of this invention.

| Example No. | Example-11 | Example-12 | Example-13 | Example-14 |
|---|---|---|---|---|
| Catalyst (III) Used | Catalyst prepared in Example-10 | Catalyst prepared in Example-10 | Catalyst prepared in Example-10 | Catalyst prepared in Example-10 |
| Catalyst pre-treatment condition | Same as that in Example-1 | Same as that in Example-1 | Same as that in Example-1 | Same as that in Example-1 |
| Reactants | | | | |
| Aromatic compound (II) | Diphenyl methane | Diphenyl methane | n-Butyl benzene | n-Butyl benzene |
| Gas comprising oxygen | Pure oxygen | Pure oxygen | Pure oxygen | Pure oxygen |
| Reaction conditions | | | | |
| Solvent/II wt. ratio | 0.0 | 0.0 | 0.0 | 0.0 |
| II/III wt. ratio | 10 | 10 | 10 | 6 |
| Temperature (° C.) | 135 | 185 | 150 | 140 |
| Pressure (atm) | 1.4 | 10.0 | 2.5 | 1.6 |
| Reaction period (h) | 20 | 1 | 5 | 10 |
| Main product i.e. Aromatic carbonyl compound (I) formed | Benzo-phenone | Benzo-phenone | n-Butyro-phenone | n-Butyro-phenone |
| Conversion of II (%) | 50.6 | 45.6 | 30.1 | 31.3 |
| Selectivity for I (%) | 99.8 | 99.5 | 95.2 | 95.7 |

TABLE 4

Results of the oxidation of said aromatic compound (II) in the process of this invention.

| Example No. | Example-15 | Example-16 | Example-17 | Example-18 |
|---|---|---|---|---|
| Catalyst (III) Used | Catalyst prepared in Example-10 | Catalyst prepared in Example-10 | Catalyst prepared in Example-10 | Catalyst prepared in Example-10 |
| Catalyst pre-treatment condition | Same as that in Example-1 | Same as that in Example-1 | Same as that in Example-1 | Same as that in Example-1 |
| Reactants | | | | |
| Aromatic compound (II) | 4-Ethyl toluene | Benz-hydrol | 1-Ethyl naph-thalene | n-propyl benzene |
| Gas comprising oxygen | Pure oxygen | Pure oxygen | Pure oxygen | Pure oxygen |
| Reaction conditions | | | | |
| Solvent | Nil | m-Xylene | m-Xylene | Nil |
| Solvent/II wt. ratio | 0.0 | 5.0 | 3.0 | 0.0 |
| II/III wt. ratio | 10 | 7 | 12 | 8 |
| Temperature (° C.) | 140 | 130 | 130 | 150 |
| Pressure (atm) | 1.5 | 7.5 | 1.6 | 1.8 |
| Reaction period (h) | 5 | 20 | 15 | 5 |
| Main product i.e. Aromatic carbonyl compound (I) formed | 4-Methyl aceto-phenone | Benzo-phenone | 1-Aceto-naphthone | Propio-phenone |
| Conversion of II (%) | 35.7 | 77.9 | 49.8 | 20.3 |
| Selectivity for I (%) | 98.5 | 99.9 | 98.7 | 90.7 |

Examples 19–22

These examples further illustrate the process of this invention for the oxidation of ethyl benzene to acetophenone, n-propyl benzene to propiophenone, n-butyl benzene to n-butyrophenone and diphenyl methane to benzophenone with continuous removal of the reaction water during the oxidation reaction, using the catalyst prepared in Example-1.

The catalytic oxidation reactions were carried out, by the method similar to that described in Example-1 except that a Dean-Stark trap was used between the reactor and the reflux condenser, each of the reactions is carried out with or without using a non-aqueous solvent, each of the reactions was carried out under reflux and the water formed in each of the reactions was removed continuously during the reaction. The results obtained are given in Table 5.

TABLE 5

Results of the oxidation of said aromatic compound (II) in the process of this invention.

| Example No. | Example-19 | Example-20 | Example-21 | Example-22 |
|---|---|---|---|---|
| Catalyst (III) Used | Catalyst prepared in Example-1 | Catalyst prepared in Example-1 | Catalyst prepared in Example-1 | Catalyst prepared in Example-1 |
| Catalyst pre-treatment condition | Same as that in Example-1 | Same as that in Example-1 | Same as that in Example-1 | Same as that in Example-1 |
| Reactants | | | | |
| Aromatic compound (II) | Ethyl benzene | n-Propyl benzene | n-Butyl benzene | Diphenyl methane |
| Gas comprising oxygen | Pure oxygen | Pure oxygen | Pure oxygen | Pure oxygen |
| Reaction conditions | | | | |
| Solvent used | Nil | Nil | m-Xylene | p-Xylene |
| Solvent/II wt. ratio | 0.0 | 0.0 | 2.0 | 5.0 |
| II/III wt. ratio | 10 | 8 | 6 | 5 |
| Temperature (° C.) | Under reflux | Under reflux | Under reflux | Under reflux |
| Pressure (atm) | 1.8 | 1.5 | 1.5 | 1.9 |
| Reaction period (h) | 20 | 20 | 20 | 20 |
| Main product i.e. Aromatic carbonyl compound (I) formed | Aceto-phenone | Propio-phenone | n-Butyro-phenone | Benzo-phenone |
| Conversion of II (%) | 91.0 | 45.6 | 60.2 | 90.2 |
| Selectivity for I (%) | 97.1 | 86.3 | 90.1 | 98.1 |

Example 23

This example further illustrates the process of this invention for the oxidation of ethyl benzene to acetophenone using a hydrotalcite-like catalyst, containing $MnO_4^{1-}$ anions at concentration 0.45 mmol.g$^{-1}$, derived from a hydrotalcite-like material having chemical formula same as that in Example-1 except that x was 0.33 instead of 0.25.

The hydrotalcite-like material, with x=0.33, was prepared by the method similar to that described in Example-1 except that the amount of aluminum nitrate was 0.45 mol instead of 0.3 mol.

The hydrotalcite-like catalyst was prepared from the hydrotalcite-like material by the method similar to that described in Example-1 except that the amount of $KMnO_4$ was 0.01 mol instead of 0.12 mol. The concentration of $MnO_4^{1-}$ anions in the catalyst was 0.45 mmol.g$^{-1}$. The XRD data of both the hydrotalcite-like material and the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.

Conversion of ethyl benzene : 25.6%
Selectivity for acetophenone : 99.5%

Example 24

This example further illustrates the process of this invention for the oxidation of ethyl benzene to acetophenone using a hydrotalcite-like catalyst, containing $MnO_4^{1-}$ anions at concentration 1.2 mmol.g$^{-1}$, derived from a hydrotalcite-like material having chemical formula same as that in Example-1 except that the trivalent cation was $Fe^{3+}$ instead of $Al^{3+}$.

The hydrotalcite-like material was prepared by the method similar to that described in Example-1 except that 0.3 mol ferric nitrate was used instead of 0.3 mol aluminum nitrate.

The hydrotalcite-like catalyst was prepared from the hydrotalcite-like material by the method similar to that described in Example-1 except that the amount of $KMnO_4$ was 0.04 mol instead of 0.12 mol. The concentration of $MnO_4^{1-}$ anions in the catalyst was 1.2 mmol.g$^{-1}$. The XRD data of both the hydrotalcite-like material and the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.

Conversion of ethyl benzene : 31.3%
Selectivity for acetophenone : 99.2%

Example 25

This example further illustrates the process of this invention for the oxidation of ethyl benzene to acetophenone using a hydrotalcite-like catalyst, containing $MnO_4^-$ anions at concentration 1.5 mmol.g$^{-1}$, derived from a hydrotalcite-like material having chemical formula same as that in Example-24 except that the trivalent cation was $Ga^{3+}$ instead of $Fe^{3+}$.

The hydrotalcite-like material was prepared by the method similar to that described in Example-24 except that 0.3 mol gallium nitrate was used instead of 0.3 mol ferric nitrate.

The hydrotalcite-like catalyst was prepared from the hydrotalcite-like material by the method similar to that described in Example-24, The concentration of $MnO_4^{1-}$ anions in the catalyst was 1.5 mmol.g$^{-1}$. The XRD data of both the hydrotalcite-like material and the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.

Conversion of ethyl benzene : 36.5%
Selectivity for acetophenone : 99.3%

Example 26

This example further illustrates the process of this invention for the oxidation of ethyl benzene to acetophenone using a hydrotalcite-like catalyst, containing $Cr_2O_7^{2-}$ anions at concentration 0.9 mmol.g$^{-1}$, derived from a hydrotalcite-like material having chemical formula same as that in Example-1.

The hydrotalcite-like material was prepared by the method similar to that described in Example-1.

The hydrotalcite-like catalyst was prepared from the hydrotalcite-like material by the method similar to that described in Example-1 except that 0.04 mol $K_2Cr_2O_7$ was used instead of 0.12 mol $KMnO_4$. The concentration of $Cr_2O_7^{2-}$ anions in the catalyst was 0.9 mmol.g$^{-1}$. The XRD data of the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.
Conversion of ethyl benzene : 37.8%
Selectivity for acetophenone : 99.2%

Example 27

This example further illustrates the process of this invention for the oxidation of ethyl benzene to acetophenone using a hydrotalcite-like catalyst, containing $CrO_4^{2-}$ anions at concentration 1.1 mmol.g$^{-1}$, derived from a hydrotalcite-like material having chemical formula same as that in Example-1.

The hydrotalcite-like material was prepared by the method similar to that described in Example-1.

The hydrotalcite-like catalyst was prepared from the hydrotalcite-like material by the method similar to that described in Example-26 except that 0.05 mol $K_2CrO_4$ was used instead of 0.04 mol $K_2Cr_2O_7$. The concentration of $K_2CrO_4^{2-}$ anions in the catalyst was 1.1 mmol.g$^{-1}$. The XRD data of the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.
Conversion of ethyl benzene : 28.3%
Selectivity for acetophenone : 99.6%

Example 28

This example further illustrates the process of this invention for the oxidation of ethyl benzene to acetophenone using a hydrotalcite-like catalyst, containing $SeO_4^{2-}$ anions at concentration 1.2 mmol.g$^{-1}$, derived from a hydrotalcite-like material having chemical formula same as that in Example-1.

The hydrotalcite-like material was prepared by the method similar to that described in Example-1.

The hydrotalcite-like catalyst was prepared from the hydrotalcite-like material by the method similar to that described in Example-1 except that 0.04 mol $Na_2SeO_4$ was used of 0.12 $KMnO_4$. The concentration of $SeO_4^{2-}$ anions in the catalyst was 1.2 mmol.g$^{-1}$. The XRD data of the hydrotalcite-like catalyst were similar to that of the hydrotalcite material prepared in Example-1.

The catalytic oxidation of ethyl benzene over the hydrotalcite-like catalyst was carried out by the method and reaction conditions same as that used in Example-1. The conversion and product selectivity were as follows.
Conversion of ethyl benzene : 41.3%
Selectivity for acetophenone : 98.5%

Example 29

This example further illustrates the process of this invention for the oxidation of benzyl alcohol to benzaldehyde using a hydrotalcite-like catalyst, containing $MoO_4^{2-}$ anions at concentration 1.3 mmol.g$^{-1}$, derived from a hydrotalcite-like material having chemical formula same as that in Example-1 except that the divalent cation was $Ni^{2+}$ instead of $Mg^{2+}$.

The hydrotalcite-like material was prepared by the method similar to that described in Example-1 except that 0.9 mol nickel nitrate was used instead of 0.9 mol magnesium nitrate.

The hydrotalcite-like catalyst was prepared from the hydrotalcite-like material by the method similar to that described in Example-1 except that 0.04 mol $Na_2MoO_4$ was used instead of 0.12 mol $KMnO_4$. The concentration Of $MoO_4^{2-}$ anions in the catalyst was 1.3 mmol.g$^{-1}$. The XRD data of both the hydrotalcite-like material and the hydrotalcite-like catalyst were similar to that of the hydrotalcite material prepared in Example-1.

The catalytic oxidation of benzyl alcohol over the hydrotalcite-like catalyst was carried out by the method and reaction conditions same as that used in Example-1 except that the reaction was carried out under reflux at 204° C. and oxygen gas was bubbled continuously through the reaction mixture at a flow rate of 6 ml per min at atmospheric pressure, 1.0 atm. The conversion and product selectivity were as follows.
Conversion of benzyl alcohol : 25.9%
Selectivity for benzaldehyde : 89.2%

Example 30

This example further illustrates the process of this invention for the oxidation of benzyl alcohol to benzaldehyde using a hydrotalcite-like catalyst, containing $WO_4^{2-}$ anions at concentration 1.1 mmol.g$^{-1}$, derived from a hydrotalcite-like material having chemical formula same as that in Example-1.

The hydrotalcite-like material, with x=0.09, was prepared by the method similar to that described in Example-1.

The hydrotalcite-like catalyst was prepared from the hydrotalcite-like material by the method similar to that described in Example-1 except that 0.05 mol $Na_2WO_4$ was used instead of 0.12 mol $KMnO_4$. The concentration Of $WO_4^{2-}$ anions in the catalyst was 1.1 mmol.g$^{-1}$. The XRD data of the hydrotalcite-like catalyst is similar to that of the hydrotalcite material prepared in Example-1.

The catalytic oxidation of benzyl alcohol over the hydrotalcite-like catalyst was carried out by the method and reaction conditions same as that used in Example-29 except that the reaction period was 5 h. The conversion and product selectivity were as follows.
Conversion of benzyl alcohol : 25.2%
Selectivity for benzaldehyde : 93.7%

Examples 31 to 34

These examples further illustrate the process of the invention for the oxidation benzyl alcohol using $CrO_4^{2-}$ and $Cr_2O_7^{2-}$ anions containing hydrotalcite-like catalysts prepared in Examples 26 and 27, respectively.

The process was carried by the method similar to that described in Example-30 except that the catalyst pretreatment and reaction conditions were different, as given in Table-6. The results of the oxidation are given in Table-6.

TABLE 6

Results of the oxidation of benzyl alcohol to benzaldehyde in the process of this invention.

| Example No. | Example-31 | Example-32 | Example-33 | Example-34 |
|---|---|---|---|---|
| Catalyst (III) Used | Catalyst prepared in Example-26 | Catalyst prepared in Example-27 | Catalyst prepared in Example-27 | Catalyst prepared in Example-26 |
| Catalyst pre-treatment condition | In pure nitrogen at 200° C. for 1 h | Under vacuum at 100° C. for 10 h | In $CO_2$-free air at 100° C. for 20 h | Under vacuum at 150° C. for 3 h |
| Reactants | | | | |
| Aromatic compound (II) | Benzyl alcohol | Benzyl alcohol | Benzyl alcohol | Benzyl alcohol |
| Gas comprising oxygen | Pure oxygen | Pure oxygen | Pure oxygen | Pure oxygen |
| Reaction conditions | | | | |
| Solvent/II wt. ratio | 0.0 | 0.0 | 00 | 2.0ª |
| II/III wt. ratio | 50.0 | 40.0 | 20.0 | 20.0 |
| Temperature (° C.) | 205 | 180 | 201 | 105 |
| Pressure (atm) | 1.0 | 1.0 | 1.0 | 1.0 |
| Reaction period (h) | 5.0 | 5.0 | 15.0 | 5.0 |
| Main product i.e. Aromatic carbonyl compound (I) formed | Benzaldehyde | Benzaldehyde | Benzaldehyde | Benzaldehyde |
| Conversion of II (%) | 19.6 | 25.9 | 47.5 | 11.5 |
| Selectivity for I (%) | 99.8 | 98.7 | 95.9 | 99.7 |

Advantages of Present Invention

1. The present invention uses hydrotalcite-like solid catalyst containing said polyoxometallate anions, which are active catalytic components.
2. In the present invention, the catalytically active components, polyoxometallate anions, which are negatively charged, are bond to positively charged surface by chemical attractive forces and hence there is no leaching of catalytically active components from the catalyst during the oxidation reaction.
3. The catalyst of the present invention can be easily separated, simply by filtration, and also can be reused in the process repeatedly.
4. In the process of present invention, the catalyst shows high activity in the oxidation of —$CH_2$— or —CHOH— group attached to aromatic nucleus, producing corresponding aromatic carbonyl compound with high selectivity.
5. The process of present invention does not produce any toxic and/or corrosive by-product. The by-product formed in the present process is water, which is environmentally benign.
6. The process of present invention does not require costly reagent. The oxidizing agent used in the present process is molecular oxygen, which is much cheaper than acylating agent(s) used in the prior art acylation processes.
7. The process of present invention can be carried out in the absence of any solvent, while achieving high conversion of aromatic reactant into corresponding aromatic carbonyl compound.
8. The process of present invention can be carried out even at or close to atmospheric pressure with high conversion of aromatic reactant into corresponding aromatic carbonyl compound and hence the oxidation process of present invention is much less hazardous.
9. The process of present invention is environmentally much greener or benign.
10. The process of this invention can be used in chemical industries for the production of aromatic carbonyl compounds, such as aromatic phenones, for example: acetophenone from ethyl benzene, benzophenone from diphenyl methane or benzhydrol, propinophenone from propyl benzene, butyrophenone from butyl benzene, etc and aromatic aldehydes, for example: benzaldehyde from benzyl alcohol, substituted benzaldehyde from substituted benzyl alcohol, etc.

What is claimed is:

1. A process for the preparation of aromatic carbonyl compounds of general formula (I)

Ar—CO—R  Formula (I)

Ar represents an aromatic nucleus with one or more aromatic rings

R is defined as hydrogen group (—H), paraffine group (—$C_nH_{2n+1}$) wherein, n is an integer more than or equal to 1), substituted paraffine groups, cycloparaffine group (—$C_mH_{2m-1}$) wherein, m is an integer greater than 2), substituted cycloparaffine group, substituted or unsubstituted aromatic nucleus containing one or more aromatic rings, by liquid phase catalytic oxidation, said process comprising the steps of:
(a) pretreating a polyoxometallate anion exchanged hydrotalcite catalyst under a vacuum or gas atmosphere free from traces of moisture and carbon-dioxide at a temperature in the range 50–200° C., for a period sufficient to remove adsorbed moisture from the catalyst;
(b) oxidizing an aromatic compound of general formula (II) in the presence of the pretreated polyoxometallate anion exchanged hydrotalcite catalyst

Ar—CHX—R  Formula (II)

wherein,
Ar and R are as defined above
X is hydrogen group (—H) or hydroxyl (—OH) group,
(c) separating the products (I) from the reaction mixture;
(d) washing the used catalyst by aromatic compound (II) or optionally washing the catalyst by non aqueous solvent and drying the washed catalyst; and
(e) recycling the catalyst for subsequent reaction batch.

2. The process of claim 1, wherein in step (b) the polyoxometallate anion exchanged hydrotalcite catalyst is obtained from a hydrotalcite catalyst (IV) represented by a general formula:

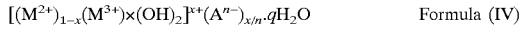

$[(M^{2+})_{1-x}(M^{3+})_x(OH)_2]^{x+}(A^{n-})_{x/n}\cdot qH_2O$  Formula (IV)

wherein
$M^{2+}$ is divalent metal cation, $M^{3+}$ is trivalent metal cation, x is mole fraction of $M^{3+}$ between $M^{2+}$ and $M^{3+}$ in the range of 0.06–0.4, $A^{n-}$ is anion selected from $CO_3^{2-}$, $OH^{1-}$, $Cl^-$, $NO_3^{1-}$ or a mixture thereof, n is an integer showing number of negative charges on the anion ($A^{n-}$), q is number of water molecules, by (a) replacing the $A^{n-}$ anions from said hydrotalcite material (IV) at least partly by polyoxometallate anions in a gaseous atmosphere of oxygen, at a temperature in the range of 50–300° C. and pressure of about 1.0 atmosphere, in the presence of a solvent for a period of 1–100 hours;

(b) stirring the reaction mixture in a reactor and cooling the reactor temperature to about 30° C.;

(c) depressurizing the reactor; and (d) removing the polyoxometallate anion exchanged hydrotalcite catalyst from the reaction mixture by filtration.

3. The process of claim 2, wherein polyoxometallate anions are selected from $(MnO_4)^{1-}$, $(Cr_2O_7)^{2-}$, $(CrO_4)^{2-}$, $(WO_4)^{2-}$, $(MoO_4)^{2-}$, $(SeO_4)^{2-}$, $(VO_3)^{1-}$, $(VO_4)^{3-}$ and a mixture thereof.

4. The process of claim 2, wherein the concentration of the polyoxometallate anions in the catalyst is in the range from 0.05–5.0 mmol.g$^{-1}$.

5. The process of claim 1, wherein the usage of solvent is optional.

6. The process of claim 5, wherein in step (b) the solvent and aromatic compound (II) weight ratio is in the range 0–50.

7. The process of claim 1, wherein in step (b) weight ratio of aromatic compound (II) with the polyoxometallate anion exchanged hydrotalcite catalyst is in the range 1:100.

8. The process of claim 1, wherein in step (b) continuous removal of water formed during oxidation of aromatic compound (II) is optional.

9. The process of claim 1, wherein in step (b) the stirring process in the reactor is done in batch mode or in semi-batch mode or in continuous mode.

10. The process of claim 1, wherein the reaction temperature in step (b) is in the range of 100–250° C.

11. The process of claim 1, wherein the reaction period in step (b) is in the range of 1–20 hours.

12. The process of claim 1, wherein the aromatic nucleus is selected from a group consisting of benzene, naphthalene, anthracene and phenanthrene.

13. The process of claim 1, wherein the aromatic nucleus may be substituted or unsubstituted.

14. The process of claim 13, wherein the substitution on the aromatic nucleus is selected from the group consisting of paraffin ($C_nH_{2n+1}$) or substituted paraffin, cycloparaffin ($C_mH_{2m-1}$) or substituted cycloparaffin, and phenyl ($C_6H_5$).

15. The process of claim 14, wherein substituted phenyl groups are selected from halo (F, Cl, Br or I), nitro ($NO_2$), hydroxyl (OH), ketonic (COR), sulfonic acid ($HSO_3$), alkoxy ($OC_nH_{2n+1}$), phenoxy ($OC_6H_5$) or substituted phenoxy, ester ($COOC_nH_{2n+1}$), and carboxylic acid (COOH), wherein n and m having values 1 or 2.

16. The process of claim 2, wherein $M^{2+}$ in the hydrotalcite material (IV) is selected from $Mg^{2+}$, $Ni^{2+}$, $Co^{2+}$, $Cu^{2+}$, $Zn^{2+}$, $Mn^{2+}$, $Pd^{2+}$ or a mixture of thereof.

17. The process of claim 16, wherein $M^{2+}$ in the hydrotalcite material (IV) is $Mg^{2+}$, $Ni^{2+}$, $Co^{2+}$ or a mixture thereof.

18. The process of claim 2, wherein $M^{3+}$ in the hydrotalcite material (IV) is selected from $Al^{3+}$, $Fe^{3+}$, $Ga^{3+}$, $In^{3+}$, $Cr^{3+}$, $Ru^{3+}$ or a mixture thereof.

19. The process of claim 18, wherein $M^{3+}$ in the hydrotalcite-like material (IV) is $Al^{3+}$ or $Fe^{3+}$ or $Ga^{3+}$ or a mixture thereof.

20. The process of claim 2, wherein the mole fraction of $M^{3+}$ and x in the hydrotalcite material (IV) is in the range of 0.09 and 0.33.

21. The process of claim 2, wherein $A^{n-}$ anion in the hydrotalcite material (IV) is $CO_3^{2-}$.

22. The process of claim 1, wherein the concentration of polyoxometallate anions in the polyoxometallate anion exchanged hydrotalcite catalyst is between 0.3 mmol.g$^{-1}$ and 4.0 mmol.g$^{-1}$.

* * * * *